Figure 1:
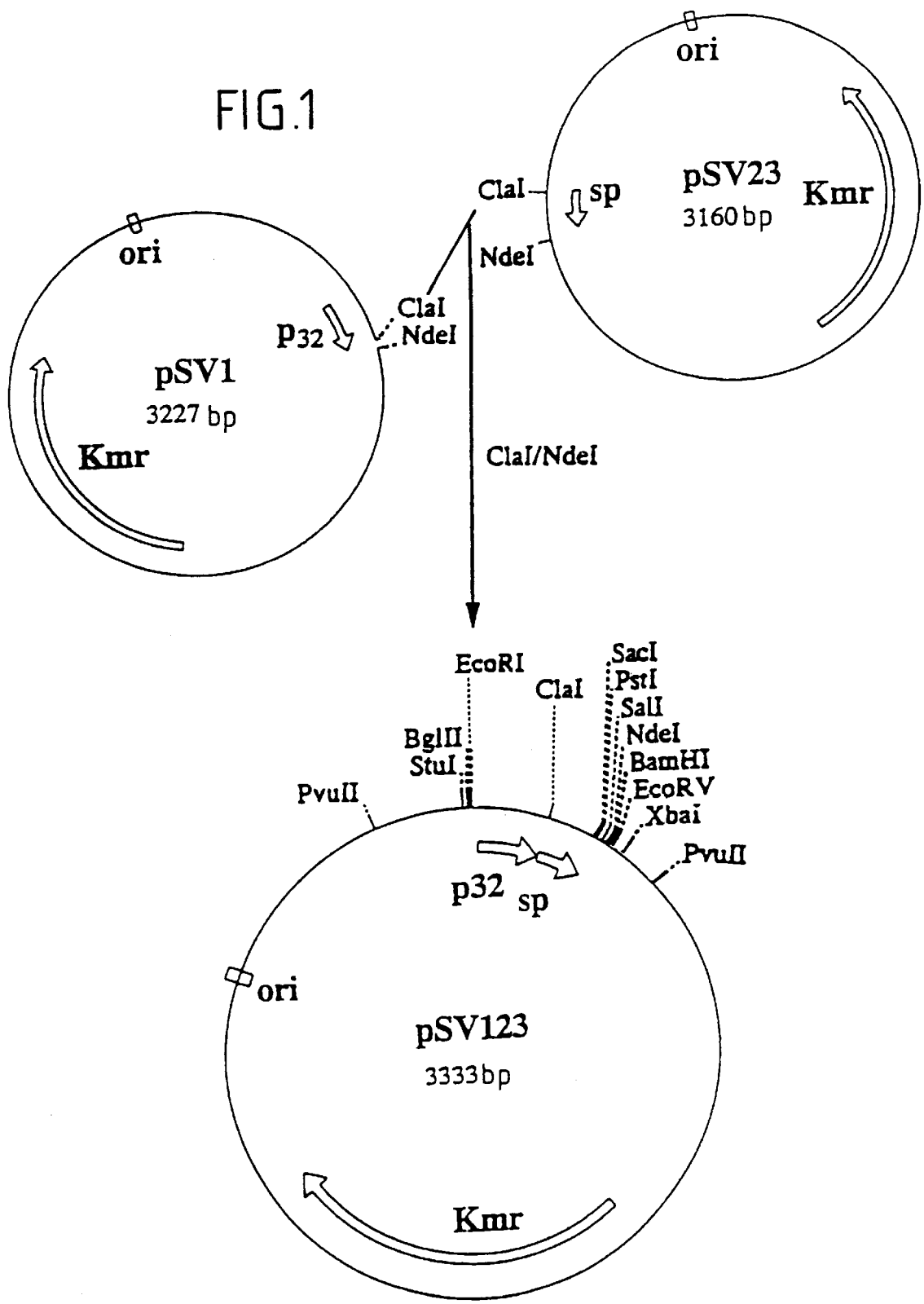

United States Patent [19]
Fayard et al.

[11] Patent Number: 5,939,317
[45] Date of Patent: Aug. 17, 1999

[54] USE OF A SEC-DEPENDENT SECRETION SYSTEM FOR SECRETING PROTEINS THAT ARE USUALLY SECRETED BY A SEC-INDEPENDENT SECRETION SYSTEM, BACTERIA CONTAINING IT AND THEIR USE

[75] Inventors: Blandine Fayard, Drieborg; Jan Kok, Groningen; Gerhardus Venema, Haren, all of Netherlands; Marc Bigret, Le Perreux; Fabien Prevots, Toulouse, both of France

[73] Assignee: SKW Biosystems, France

[21] Appl. No.: 08/849,373

[22] PCT Filed: Oct. 7, 1996

[86] PCT No.: PCT/FR96/01560

§ 371 Date: Jun. 6, 1997

§ 102(e) Date: Jun. 6, 1997

[87] PCT Pub. No.: WO97/13863

PCT Pub. Date: Apr. 17, 1997

[30] Foreign Application Priority Data

Oct. 6, 1995 [FR] France .................................. 95 11778

[51] Int. Cl.⁶ .......................... C12N 15/63; C12N 15/11; C07H 21/04
[52] U.S. Cl. .......................... 435/320.1; 435/6; 435/69.1; 435/172.3; 435/252.9; 536/23.1; 536/23.7; 536/24.1
[58] Field of Search ........................ 435/6, 69.1, 172.1, 435/172.3, 252.9, 243, 320.1; 536/23.1, 23.4, 23.7, 24.1

[56] References Cited

FOREIGN PATENT DOCUMENTS

| | | |
|---|---|---|
| 0244042 | 11/1987 | European Pat. Off. . |
| 0455280 | 11/1991 | European Pat. Off. . |
| 91/19802 | 12/1991 | WIPO . |
| 92/04451 | 3/1992 | WIPO . |

OTHER PUBLICATIONS

Oliver et al. "SecA protein: Autoregulated ATPase Catalysing Preprotein Insertion and Translocation Across the *Eschericia coli* Inner Membrane" Molecular Microbiology vol. 7(2): 159–165, 1993.

M. van de Guchte, "Gene Expression in *Lactococcus lactis*", FEMS Microbiology Reviews, vol. 88, 1992, pp. 73–92.

J. Kok, et al., "Nucleotide Sequence of the Cell Wall Proteinase Gene of *Streptococcus cremoris* Wg2", Applied and Environmental Microbiology, vol. 54, No. 1, Jan. 1988, pp. 231–238.

M. van Belkum, et al., "Cloning, Sequencing, and Expression in *Escherichia coli* of IcnB, a Third Bacteriocin Determinant from the Lactococcal Bacteriocin Plasmid p9B46", Applied and Environmental Microbiology, vol. 58, No. 2, Feb. 1992, pp. 572–577.

O.P. Kuipers, et al., "Expression of Wild–Type and Mutant Nisin Genes in *Lactococcus lactis*", Editor: G. Jung, et al., "Nisin and Novel Lantibiotics", Proceedings of the First International Workshop on Lantibiotics, Apr. 15–18, 1991, pp. 250–258.

*Primary Examiner*—Nancy Degen
*Assistant Examiner*—Sean McGarry
*Attorney, Agent, or Firm*—Ostrolenk, Faber, Gerb & Soffen, LLP

[57] ABSTRACT

The invention relates to the use of a Sec-dependent secretion system for secreting proteins normally secreted by a Sec-independent secretion system.

14 Claims, 3 Drawing Sheets

USE OF A SEC-DEPENDENT SECRETION SYSTEM FOR SECRETING PROTEINS THAT ARE USUALLY SECRETED BY A SEC-INDEPENDENT SECRETION SYSTEM, BACTERIA CONTAINING IT AND THEIR USE

The present invention relates to the use of a Sec-dependent secretion system for secreting proteins normally secreted by a Sec-independent secretion system. It further relates to the lactic acid bacteria containing this Sec-dependent secretion system, in particular the *lactococci* belonging to the species *Lactococcus lactis*, to the use of certain strains of these *lactococci* for transferring said secretion system to strains of industrial interest, particularly in the dairy industry, and to the use of certain strains of *Lactococcus lactis* for obtaining this secretion system.

The secretion of proteins in bacteria generally follows two pathways. The better known is Sec-dependent transport. According to this pathway, the protein is exported by virtue of the presence, in the N-terminal position, of a signal peptide which is cleaved in the secreted protein. Several proteins involved in this secretion, particularly SecA, SecY and SecE, have been identified in *E. coli*. The *secY* gene has been identified in *L. lactis*: it possesses a high degree of homology with the *secY* gene of *E. coli*, indicating that this secretion system is very probably also present in *L. lactis* (Koivula et al., 1991, FEBS Lett. 228: 114–118).

The second secretion pathway in bacteria, which does not depend on the Sec proteins, involves transmembrane translocators called the A, B, C family of proteins (Pugsley, 1993, Microbiol. Rev. 57: 50–108).

Translocators have been identified in *L. lactis*; they are involved in the secretion of the bacteriocins LcnA, LcnB and LcnM1 and the antibiotics lacticin 481, nisin A and nisin Z (de Vos and Simons, Genetics and Biotechnology of L.A.B., Blackie Academic and Professional, 1994).

The study of these two secretion pathways in *L. lactis* has been utilized to develop different systems for the secretion of heterologous proteins. The secretion vectors developed are all contained in the review by de Vos and Simons, Genetics and Biotechnology of L.A.B., Blackie Academic and Professional, 1994.

The bacteriocins identified in lactic acid bacteria are virtually all secreted by the Sec-independent system (Dodd and Gasson, Genetics and Biotechnology of L.A.B., Blackie Academic and Professional, 1994). However, in the interest of increasing the secretion of these bacteriocins, it can be important to cause secretion of these bacteriocins by a different secretion system.

Some authors have recently shown that divergicin A, a bacteriocin produced by *Carnobacterium divergens*, is secreted via a Sec-dependent system (Worobo et al., J. Bacteriol. 177: 3143–3149). However, it has never been shown in lactic acid bacteria that a bacteriocin secreted by a Sec-independent system can be secreted by a Sec-dependent system.

The Applicant has carried out studies in this field and has found, surprisingly, that a Sec-dependent secretion system can be used to secrete proteins normally secreted by a Sec-independent secretion system.

According to the invention, the Sec-dependent secretion system is used in combination with the DNA sequence coding for a mature protein normally secreted by a Sec-independent system, and with an appropriate promoter, an appropriate signal sequence recognized by the Sec-dependent secretion system and an appropriate terminator.

Thus the invention further relates to the DNA constructions for the secretion, by a Sec-dependent system, of proteins normally secreted by a Sec-independent system, said DNA constructions comprising a promoter, a signal sequence recognized by the Sec-dependent secretion system, the DNA sequence coding for a mature protein normally secreted by a Sec-independent system, and a terminator. These DNA constructions can be present on an expression vector such as a plasmid, in the genomic DNA or in any other DNA fragment.

According to the invention, any Sec-dependent secretion system can be used in combination with a gene coding for a protein of interest which is normally secreted by a Sec-independent system.

Any Sec-dependent secretion system is suitable for the purposes of the invention. Particularly appropriate Sec-dependent secretion systems are the Sec-dependent systems of *lactococci*, which utilize in particular the sp signal sequence of the protease of *lactococcus* (PrtP protein).

Any promoters and terminators which are compatible with the host strain in which the secretion system of the invention is used can be employed according to the invention.

As examples of genes coding for a protein of interest, it is possible to use especially the genes coding for bacteriocins, in particular the bacteriocin LcnB, which is a bacteriocin secreted by *L. lactis* under the dependence of a Sec-independent secretion system (Van Belkum et al., 1992, Applied Environ. Microbiol., 58: 572–577).

Thus, in one variant, the invention relates to the expression vectors comprising a promoter, a signal sequence recognized by the Sec-dependent secretion system, the DNA sequence coding for a bacteriocin such as the bacteriocin LcnB, and a terminator.

In this variant, the promoter can advantageously be the P32 promoter of *lactococcus*, the signal sequence can be the sp signal sequence of the protease (PrtP) of *lactococcus* and the terminator can advantageously be that of the LcnB immunity gene (*ciB*).

The invention further relates to the lactic acid bacteria, preferably *L. lactis*, secreting one or more bacteriocins, which contain a construction according to the invention, as defined above, which permits the secretion of these bacteriocins. This construction can be introduced into the lactic acid bacteria by conjugation, transformation, protoplast fusion or another gene transfer method.

Examples of the lactic acid bacteria which can advantageously be transformed with the aid of the construction according to the invention are *Lactococcus lactis ssp crenioris, Lactococcus lactis ssp lactis* and *lactococcus lactis ssp lactis var diacetylactis*.

These strains transformed in this way can be used to transfer a construction according to the invention to a strain of industrial interest by conjugation, transformation, transduction, protoplast fusion or another gene transfer method. This construction can be carried by a plasmid or by another part of the bacterial genome.

The invention further relates to the strains of industrial interest which secrete proteins obtained in this way, for example bacteriocins. These bacteria which secrete bacteriocins can be used to inhibit the development of pathogenic bacteria, to lyze bacteria so that their enzyme content participates in the purification of the products fermented by these bacteria, or to have bacteria for any purpose involving a secretion of bacteriocins by a construction according to the invention.

The invention will be understood more clearly with the aid of the illustrative Examples below, which do not imply a limitation.

The bulk of the techniques described in these Examples, which are well known to those skilled in the art, are described in detail in the work by Sambrook, Fritsch and Maniatis: "Molecular cloning; a laboratory manual", published in 1989 by Cold Spring Harbor Press, N.Y. (2nd edition).

The following description will be understood more clearly with the aid of FIGS. 1 to 3 below, which respectively show:

FIG. 1: Construction of vector pSV123

Figure 2:
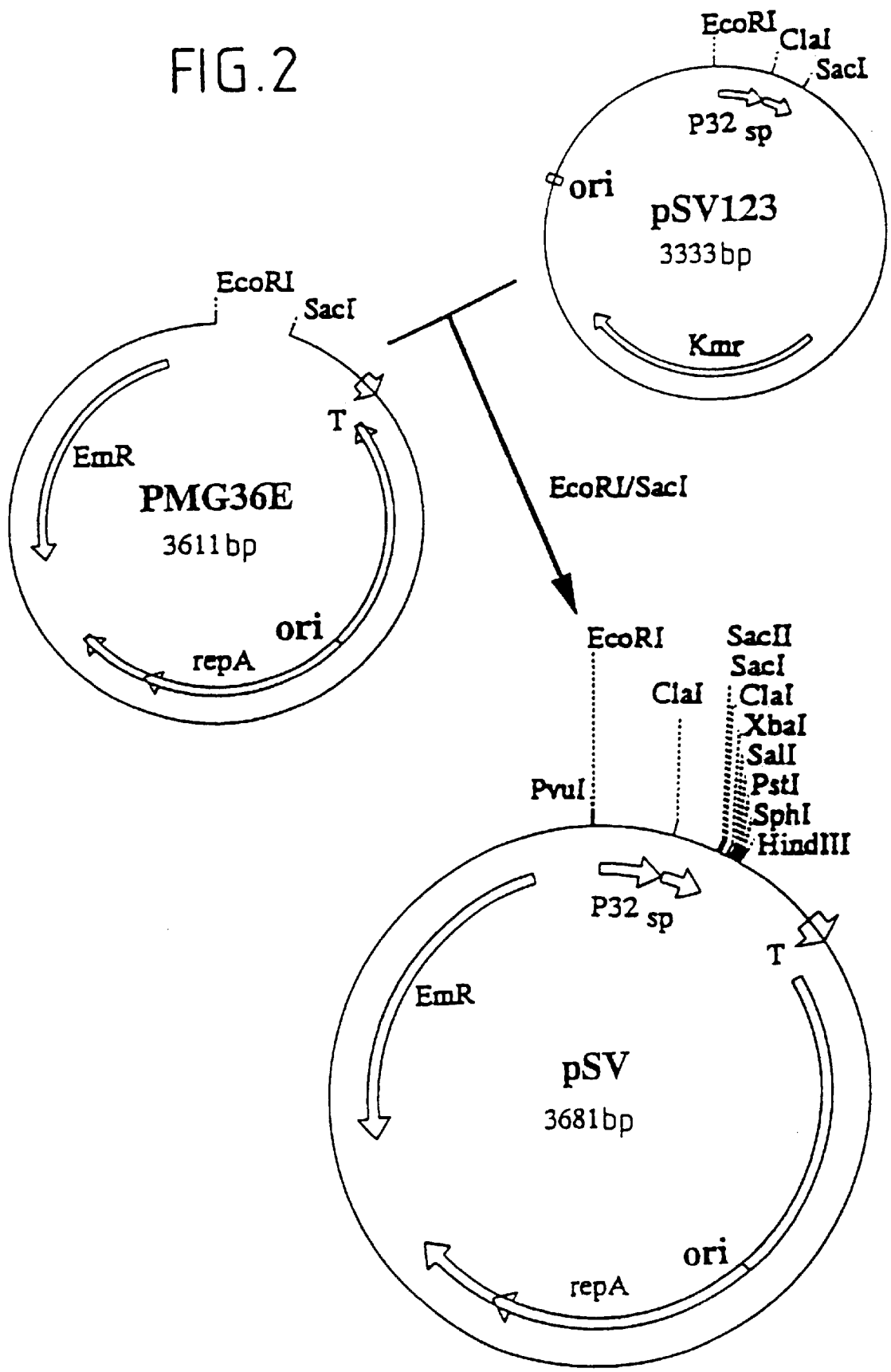

FIG. 2: Construction of secretion vector pSV

Figure 3:
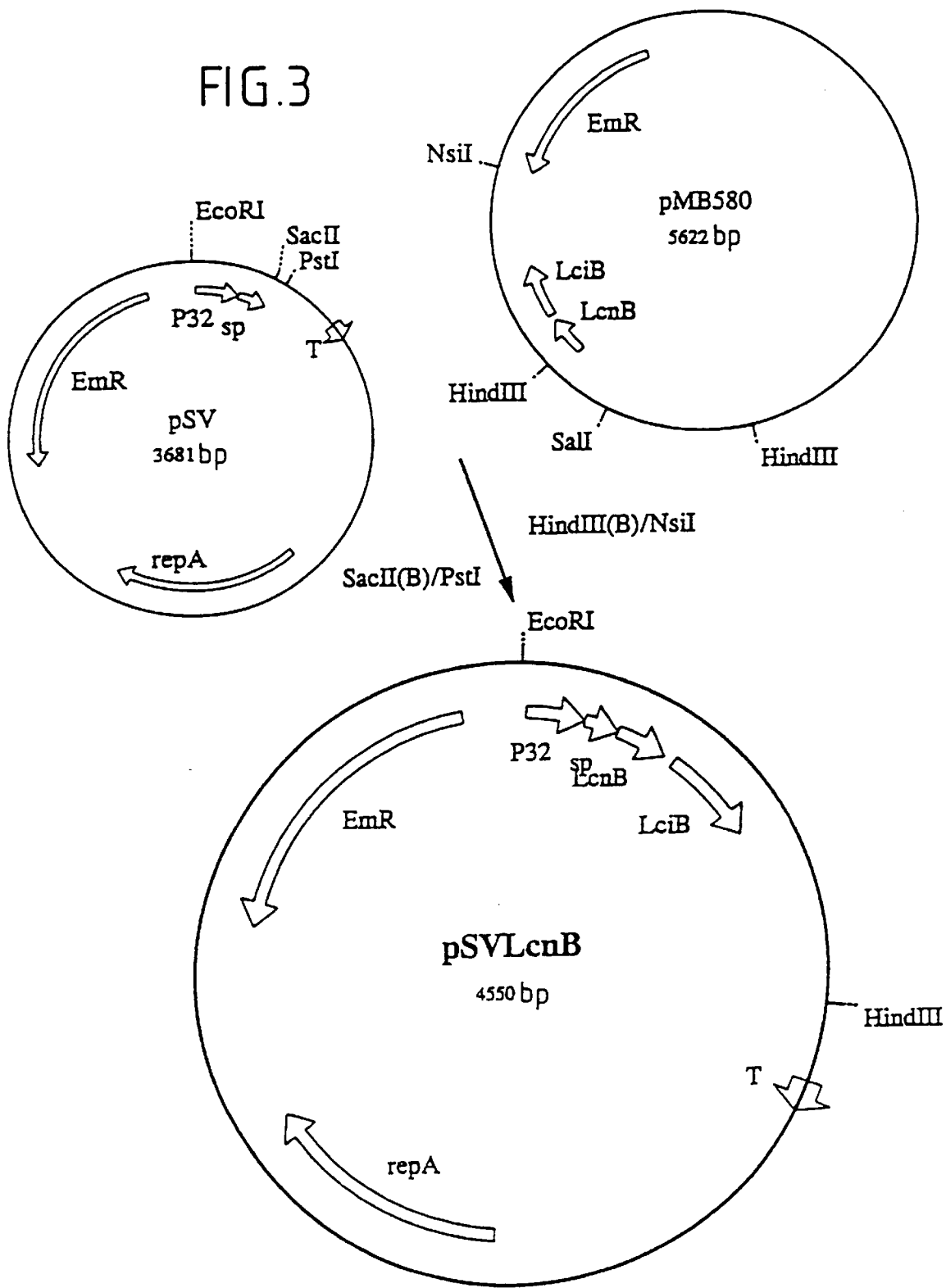

FIG. 3: Construction of plasmid pSVLcnB permitting the secretion of LcnB

Example 1: Construction of plasmid secretion vector pSV

To be able to secrete a bacteriocin whose secretion is Sec-independent, it was necessary first to construct a Sec-dependent secretion vector. This construction was prepared in the following manner:

For each of the clonings where is was necessary to do so, the PCR technique was used under the following conditions: 1 minute at 94° C. (denaturation), 2 minutes at 45° C. (hybridization) and 2 minutes at 73° C. (polymerization), 30 cycles. The oligonucleotides were synthesized with an Applied Biosystems 381A DNA synthesizer (Applied Biosystems).

Oligonucleotides A, B, C and D were used to construct secretion vector pSV.

The sequences of these oligonucleotides are as follows (the restriction sites used for cloning are underlined and the RBS in oligonucleotide B is emboldened):

```
Oligonucleotide A (SEQ ID No 1):

BglII BglII EcoRI

5'-AGATCTAGATCTGAATTCGGTCCTCGGGATAATG-3'

Oligonucleotide B (SEQ ID No 2):

PstI PstI   ClaI       RBS

5'-CTGCAGCTGCAGCATCGATAAATTCCTCCGAATATTTTTTTACC-3'

Oligonucleotide C (SEQ ID No 3):

BglII BglII  ClaI
5'-AGATCTAGATCTATCGATGCAAAGGAAAAAGAAAGGGCTTTCGATCTTG-3'

Oligonucleotide D (SEQ ID No 4):
    PstI PstI SacI SacII
5'-CTGCAGCTGCAGAGCTCGCCGCGGCCTTTGCTTGGATTTCGCCG-3'
```

PCR (polymerase chain reaction) products containing the promoter and the ribosome binding site, RBS, of ORF32 (open reading frame) were obtained from plasmid pMG36c (Van de Guchte et al., 1989, Applied Environ. Microbiol., 55: 224–228), which is derived from plasmid pMG36e used below.

The sp signal sequence of the protease of *lactococcus*, PrtP, was obtained from the *prtP* gene present in plasmid pGKV500 (Kok et al., 1988, Applied Environ. Microbiol., 54: 221–228).

After digestion with the restriction enzymes BglII and PstI, these PCR products were cloned into plasmid pUK21 (Vieira and Messing, 1991, Gene, 100: 189–194) to give plasmids pSVI and pSV23 (FIG. 1). Plasmid pSV23 was then digested with the restriction enzymes to ClaI and NdeI and the fragment containing the signal sequence was cloned into plasmid pSVI, previously digested with the restriction enzymes ClaI and NdeI, to give plasmid pSV123 (FIG. 1). Finally, the EcoRI-SacI fragment of pSVI23, containing the P32 promoter and the sp signal sequence, was cloned into plasmid pMG36e (Van de Guchte et al., 1989, Applied Environ. Microbiol., SS: 224–228) to give secretion vector pSV (FIG. 2).

Example 2: Construction of plasmid pSVLcnB involved in the secretion of the bacteriocin LcnB Plasmid pMB580 (a plasmid conferring erythromycin resistance, derived from plasmid pGK210 and containing the operon of *lactococcin* B, i.e. LcnB and *lciB* - Van Belkum et al., 1992, Applied Environ. Microbiol., 58: 572–577) was digested with the restriction enzymes to NsiI and HindIII. The HindIII end was hydrolyzed to convert it to a blunt end. The HindIII-NsiI fragment was ligated to plasmid pSV, which had previously been digested with the restriction enzymes to PstI and SacII and whose SacII end had been hydrolyzed to convert it to a blunt end, to give plasmid pSVLcnB (FIG. 3). The resulting amino acid sequence of this LcnB derivative with the signal sequence of the PrtP protein is given below (SEQ ID N° 5):

N-MQRKKKGLSILLAGTVALGALAVLPVGEIQAKA SLQYVMSAGPYTWYKDERTGKTECKQTIDTASY-TFGVMAEGWGKTFH-C

Example 3: Secretion of LcnB by a Sec-dependent secretion system

The plasmid derived from plasmid pSV (pSVLcnB), containing the structural gene of *lactococcin* LcnB (lcnB) and the LcnB immunity gene (*lcnB*), was used to transform the strain *E. coli* JM101 (Maniatis et al., 1982, Molecular Cloning: a laboratory manual. Cold Spring Harbor, N.Y., Cold Spring Harbor Laboratory), the strain *Lactococcus lactis* MG1363 (Gasson, 1983, J. Bacteriol., 154: 1–9) and the strain *Lactococcus lactis* IL1403 (Chopin et al., 1984, Plasmid, 11: 260–263). In these constructions the N-terminal extension of the prebacteriocin was replaced with the signal peptide of PrtP (FIGS. 1, 2 and 3).

To test the bacteriocin activity, the strains were covered with an overlayer of the strain IL1043 containing either pMG36e or pMG36c. This test was performed in the following manner:

Colonies containing the construction (pSVLcnB) were incubated for 16 h at 30° C. on dishes of M17 (Terzaghi and Sandine, 1975, Appl. Microbiol., 29: 807–813)+ glucose 5 g/l+agar 5 g/l. After exposure to chloroform vapors for 20 minutes, the dishes were partially dried in air to remove the residual traces of chloroform. The following was then plated out on these dishes: 4 ml of gelose M17+glucose 5 g/l+agar 7 g/l inoculated with 40 μl of a night culture of the indicator strain *L. lactis* IL1403 containing pMG36e or pMG36c. After incubation at 30° C. for 12 to 18 h, the dishes were analyzed for the inhibition zones (halos) around the clones. The overlayer tests on tricin gels were performed according to the procedure described by Van Belkum et al., 1992, in Applied Environ. Microbiol., 58: 572–577.

The results showed that there is a halo of inhibition around the clones containing pSVLcnB. This halo is wider around the clones containing pSVLcnBc. This indicates that the bacteriocin LcnB was indeed secreted by virtue of pSVLcnB and pSVLcnBc. To confirm this result and in particular to know whether the bacteriocin activity is due to a matured form (without the sp signal peptide) or nonmatured form (with the sp signal peptide), culture supernatants of the strain IL1403 containing pSVLcnB were subjected to precipitation with ammonium sulfate and the precipitate was tested on tricin SDS-PAA electrophoresis gel. The gels were then examined for bactericidal activity. The results show that there is an inhibition of growth in the 3, 4 KDa zone corresponding to the size of the matured bacteriocin LcnB, i.e. the bacteriocin from which the sp signal sequence has been removed. As the strain *Lactococcus lactis* MG1363 does not possess the Sec-independent secretion system of bacteriocins, the bacteriocin LcnB produced by virtue of plasmid pSVLcnB was indeed secreted via the Sec-dependent secretion system using the sp signal sequence of the protease of *lactococcus*, PrtP.

We claim:

1. A DNA construct for the secretion, by a Sec-dependent system, of a protein normally secreted by a Sec-independent system, characterized in that it comprises a promoter, a signal sequence recognized by the Sec-dependent secretion system, a DNA sequence coding for a mature protein normally secreted by a Sec-independent system, and a terminator wherein said construct does not contain a multiple cloning site.

2. The construct according to claim 1, characterized in that the signal sequence recognized by the Sec-dependent secretion system is the sp signal sequence of the protease of *lactococcus*.

3. The construct according to claim 1, characterized in that the DNA sequence coding for the protein is the DNA sequence coding for a bacteriocin.

4. The construct according to claim 3, characterized in that the bacteriocin is the bacteriocin LcnB.

5. The construct according to claim 1, characterized in that the promoter is the P32 promoter of *lactococcus* and the terminator is that of the LcnB immunity gene (lciB).

6. The construct according to claim 2, characterized in that the DNA sequence coding for the protein is the DNA sequence coding for a bacteriocin.

7. The construct according to claim 6, characterized in that the bacteriocin is the bacteriocin LcnB.

8. The construct according to claim 2, characterized in that the promoter is the P32 promoter of *lactococcus* and the terminator is that of the LcnB immunity gene (lciB).

9. The construct according to claim 3, characterized in that the promoter is the P32 promoter of *lactococcus* and the terminator is that of the LcnB immunity gene (*lciB*).

10. The construct according to claim 4, characterized in that the promoter is the P32 promoter of *lactococcus* and the terminator is that of the LcnB immunity gene (*lciB*).

11. The construct according to claim 6, characterized in that the promoter is the P32 promoter of *lactococcus* and the terminator is that of the LcnB immunity gene (*lciB*).

12. The construct according to claim 7, characterized in that the promoter is the P32 promoter of *lactococcus* and the terminator is that of the LcnB immunity gene (*lciB*).

13. A process for secreting a protein that is normally secreted by a Sec-independent secretion system, using a Sec-dependent secretion system, comprising a) providing a DNA sequence coding for said protein, a promoter, a signal sequence recognized by the Sec-dependent secretion system and a terminator;

b) constructing a DNA construct comprising said DNA sequence, said promoter, said signal sequence and said terminator;

c) introducing said construct into a lactic acid bacterium by gene transfer; and d) secreting said protein by the lactic acid bacterium containing said construct.

14. The process according to claim 13, characterized in that the signal sequence is the sp signal sequence of the protease of *lactococcus*.

\* \* \* \* \*

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: YES (xi) SEQUENCE DESCRIPTION: SEQ ID NO: 1:

AGATCTAGAT CTGAATTCGG TCCTCGGGAT ATG                                 33

(2) INFORMATION FOR SEQ ID NO: 2:

(i) SEQUENCE CHARACTERISTICS:
      (A) LENGTH: 44 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: YES (xi) SEQUENCE DESCRIPTION: SEQ ID NO: 2:

CTGCAGCTGC AGCATCGATA AATTCCTCCG AATATTTTTT TACC                       44

(2) INFORMATION FOR SEQ ID NO: 3:

(i) SEQUENCE CHARACTERISTICS:
      (A) LENGTH: 49 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: YES (xi) SEQUENCE DESCRIPTION: SEQ ID NO: 3:

AGATCTAGAT CTATCGATGC AAAGGAAAAA GAAAGGGCTT TCGATCTTG                  49

-continued (2) INFORMATION FOR SEQ ID NO: 4:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 4:

CTGCAGCTGC AGAGCTCGCC GCGGCCTTTG CTTGGATTTC GCCG    44

(2) INFORMATION FOR SEQ ID NO: 5:

(i) SEQUENCE CHARACTERISTICS:
        (A) LENGTH: 80 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 5:

```
Met Gln Arg Lys Lys Lys Gly Leu Ser Ile Leu Leu Ala Gly Thr Val
1               5                   10                  15

Ala Leu Gly Ala Leu Ala Val Leu Pro Val Gly Glu Ile Gln Ala Lys
                20                  25                  30

Ala Ser Leu Gln Tyr Val Met Ser Ala Gly Pro Tyr Thr Trp Tyr Lys
            35                  40                  45

Asp Glu Arg Thr Gly Lys Thr Glu Cys Lys Gln Thr Ile Asp Thr Ala
        50                  55                  60

Ser Tyr Thr Phe Gly Val Met Ala Glu Gly Trp Gly Lys Thr Phe His
65                  70                  75                  80
```